United States Patent
Weprin et al.

(10) Patent No.: US 10,898,105 B2
(45) Date of Patent: Jan. 26, 2021

(54) MAGNETOMETER SURGICAL DEVICE

(71) Applicant: Temple University—Of The Commonwealth System of Higher Education, Philadelphia, PA (US)

(72) Inventors: Samuel Alex Weprin, Merion Station, PA (US); John Noel, Philadelphia, PA (US); Daniel D. Eun, Radnor, PA (US)

(73) Assignee: TEMPLE UNIVERSITY—OF THE COMMONWEALTH SYSTEM OF HIGHER EDUCATION, Philadelphia, PA (US)

( * ) Notice: Subject to any disclaimer, the term of this patent is extended or adjusted under 35 U.S.C. 154(b) by 346 days.

(21) Appl. No.: 15/614,885

(22) Filed: Jun. 6, 2017

(65) Prior Publication Data

US 2017/0347915 A1    Dec. 7, 2017

Related U.S. Application Data

(60) Provisional application No. 62/346,392, filed on Jun. 6, 2016.

(51) Int. Cl.
*A61B 5/06* (2006.01)
*G01V 3/08* (2006.01)
(Continued)

(52) U.S. Cl.
CPC .............. *A61B 5/062* (2013.01); *A61B 5/065* (2013.01); *A61B 5/067* (2013.01); *A61B 5/7435* (2013.01);
(Continued)

(58) Field of Classification Search
CPC .......... A61B 5/062; A61B 5/065; A61B 5/067; A61B 5/7415; A61B 5/742; A61B 5/7435;
(Continued)

(56) References Cited

U.S. PATENT DOCUMENTS

| | | |
|---|---|---|
| 4,837,489 A | 6/1989 | Mcfee |
| 5,230,338 A | 7/1993 | Allen et al. |

(Continued)

FOREIGN PATENT DOCUMENTS

| | | |
|---|---|---|
| WO | 1997045157 A1 | 12/1997 |
| WO | 2015/138708 A1 | 9/2015 |

OTHER PUBLICATIONS

Pearson, C. (Ed.). (1990). Formulas from Algebra, Trigonometry and Analytic Geometry In Handbook of Applied Mathematics (p. 65-67). New York, NY: Van Nostrand Reinhold (Year: 1990).*

(Continued)

*Primary Examiner* — Bill Thomson
*Assistant Examiner* — Younhee Choi
(74) *Attorney, Agent, or Firm* — Riverside Law, LLP

(57) ABSTRACT

A magnetometer-based metal detection device and methods of use are described. The device includes a proximal portion, a central body and a distal portion, and at least one magnetometer positioned within or on the distal portion. The at least one magnetometer includes at least one sensor capable of sensing a magnetic field in three orthogonal axes. Also described is a method of calibrating the device to achieve rotational invariance, and a method of determining a directionality or directional line along which a target metal object lies.

17 Claims, 14 Drawing Sheets

(51) Int. Cl.
*A61B 5/00* (2006.01)
*G16H 40/40* (2018.01)
*G01V 13/00* (2006.01)
*G06F 17/11* (2006.01)

(52) U.S. Cl.
CPC .............. *G01V 3/081* (2013.01); *G01V 13/00* (2013.01); *A61B 5/742* (2013.01); *A61B 5/7415* (2013.01); *A61B 2505/05* (2013.01); *A61B 2560/0223* (2013.01); *A61B 2560/0238* (2013.01); *A61B 2562/0219* (2013.01); *A61B 2562/0247* (2013.01); *G06F 17/11* (2013.01); *G16H 40/40* (2018.01)

(58) Field of Classification Search
CPC .. A61B 2017/00876; A61B 2034/2048; A61B 2505/05; A61B 2560/0223; A61B 2560/0238; A61B 2562/0247; G01V 3/081; G01V 13/00; G16H 40/40; G06F 17/11
See application file for complete search history.

(56) References Cited

U.S. PATENT DOCUMENTS

| | | | |
|---|---|---|---|
| 5,494,035 A | 2/1996 | Leuthold et al. | |
| 7,678,117 B2* | 3/2010 | Hinman | A61B 1/0055 606/108 |
| 8,352,015 B2* | 1/2013 | Bernstein | A61B 5/0402 600/424 |
| 8,392,140 B1* | 3/2013 | Bartholet | G01V 13/00 702/94 |
| 9,141,194 B1 | 9/2015 | Keyes et al. | |
| 9,427,186 B2* | 8/2016 | Hattersley | A61B 5/418 |
| 10,188,310 B2* | 1/2019 | Derichs | A61B 5/05 |
| 2007/0083107 A1 | 4/2007 | Ferre et al. | |
| 2007/0129719 A1* | 6/2007 | Kendale | A61B 1/00096 606/41 |
| 2008/0294036 A1 | 11/2008 | Hoi et al. | |
| 2011/0227569 A1 | 9/2011 | Cai et al. | |
| 2012/0130164 A1* | 5/2012 | Palese | A61B 17/52 600/104 |
| 2013/0184608 A1 | 7/2013 | Pezzi | |
| 2013/0265039 A1 | 10/2013 | Cai et al. | |
| 2014/0073903 A1* | 3/2014 | Weber | A61B 5/04009 606/34 |
| 2014/0159716 A1* | 6/2014 | McCollough, Jr. | G01R 33/0005 324/247 |
| 2014/0180267 A1* | 6/2014 | Vetter | A61B 17/320016 606/33 |
| 2014/0257081 A1 | 9/2014 | Rapoport | |
| 2014/0257104 A1* | 9/2014 | Dunbar | A61B 8/4254 600/443 |
| 2015/0141806 A1 | 5/2015 | Smith et al. | |
| 2015/0177020 A1* | 6/2015 | An | G01C 25/00 702/92 |
| 2016/0051164 A1 | 2/2016 | Derichs et al. | |
| 2016/0262844 A1 | 9/2016 | Cohen et al. | |

OTHER PUBLICATIONS

Small, Alexander C., et al. "Laparoscopic needle-retrieval device for improving quality of care in minimally invasive surgery." Journal of the American College of Surgeons 217.3 (2013): 400-405.

* cited by examiner

MAGNETOMETER SURGICAL DEVICE

CROSS-REFERENCE TO RELATED APPLICATIONS

This application claims the benefit of priority under 35 U.S.C. § 119(e) to U.S. Provisional Patent Application No. 62/346,392 filed Jun. 6, 2016, the contents of which are incorporated by reference herein in their entirety.

BACKGROUND OF THE INVENTION

Retained surgical instruments and lost needle events within the body cavity after an open surgical procedure is a well-documented issue and a continuing problem in medical practice. Even with the continued growth and application of minimally invasive robotic surgery systems and techniques, this error and potential harm to the patient, not to mention the liability of the medical practitioner and facility, in addition to unnecessary extra procedural costs amounting to upwards of several thousands of dollars created while hunting for a retained surgical instrument such as a lost needle still remains.

Lost surgical needles are seldom reported but are estimated to be many, many times more frequent than a retained surgical instrument and are typically found by the surgeon during the operation. Research involving 305 surgeons across a range of specialties indicated multiple lost needle events per year and a weighted average recovery time of 12-13 minutes. Of note, this recovery time typically results in two surgeons, an anesthesiologist, two to three nurses, surgeon assistants and an operating room & equipment being on hold while the surgeon searches. There is documented evidence of such searches taking as long as 50-60 minutes. Very quickly, several thousand dollars of extra expense is created while hunting for a lost needle. The real burden for the surgeon and surgical center is the time and expense related to the search as well as the risk to the patient posed by increased anesthesia time, x-ray exposure and operative time.

Attempts to design metal detection devices suitable for use in surgical settings have been previously described, examples of which are U.S. Pat. No. 5,230,338; US20080294036; US20120130164 and US20130184608. However, while such devices describe mechanisms for detecting magnetized metal objects within a body cavity, they all lack the ability to determine with high precision the exact location of the metal object, and they further cannot determine key features of the object, such as size, shape and orientation of the object within the body cavity. One reason for this lack of precision is their inability to properly calibrate and remove background magnetic field interference when detecting the target metal object. These existing systems remove background field values by single point measurement and subtraction algorithms. While such calibration mechanisms might be suitable for fixed position detectors, they are highly inadequate for mobile probes that are required to move and rotate three dimensionally around the subject's body cavity. Invariably, this results in an inaccurate magnetic field detection, which is critical when searching for very small objects, such as surgical needles. Further, because such devices can only remove background field values by single point measurement and subtraction algorithms, they are unable to determine the directionality or directional line on which the target metal object lies. Lastly, such devices are only capable of detecting magnetized metal objects, and lack the ability and/or sensitivity to determine the location of non-magnetized metal objects.

Without the capability of detecting details of the target object to be removed from a body cavity, the removal process can result in greater harm to the subject. For example, when a needle is lost or misplaced within the tissues or organs of a subject, it is not enough to merely determine the vicinity of the needle. Without determining the precise location, size and orientation of the needle, significant harm could be caused to the surrounding tissues by pulling the needle point and/or length of the needle body carelessly through the tissues. Further still, there is currently no metal object detection device particularly suitable for use in robotic surgical systems and settings.

Thus, there is a need in the art for an improved device and methods of detecting metal objects in a body cavity thereby reducing procedural time and costs. The present invention satisfies these needs.

SUMMARY OF THE INVENTION

A magnetometer-based metal detection device is described. The device includes a proximal portion, a central body and a distal portion, and at least one magnetometer positioned within or on the distal portion, wherein the at least one magnetometer includes at least one sensor capable of sensing a magnetic field in three orthogonal axes. In one embodiment, the distal portion is adjustable. In another embodiment, the device further includes an actuator positioned within or on the proximal portion, wherein the actuator is capable of directing movement of the adjustable distal portion. In another embodiment, the device further includes an accelerometer positioned within or on the distal portion. In another embodiment, the device further includes a permanent magnet positioned within or on the distal portion. In another embodiment, the device further includes an electromagnet positioned within or on the distal portion. In another embodiment, the device further includes a controller electrically connected to the at least one magnetometer. In another embodiment, the device further includes a user interface communicatively connected to the controller. In another embodiment, the device further includes a memory and programming logic resident on the memory, wherein the programming logic is capable of calibrating the device to achieve rotational invariance. In another embodiment, the programming logic is further capable of determining a directionality or directional line along which a target metal object lies. In another embodiment, the device further includes an accelerometer positioned within or on the distal portion, and wherein the programming logic is further capable of determining an absolute directionality or directional line, with respect to a horizontal plane, along which the target metal object lies. In another embodiment, the device is capable of detecting non-magnetic metal objects. In another embodiment, the device further includes at least one magnet capable of magnetizing a metal object in situ. In another embodiment, the device further includes a modulator capable of adjusting the sensitivity of the at least one magnetometer.

A method of calibrating a magnetometer-based metal detection device to achieve rotational invariance is also described. The method includes the steps of collecting raw magnetic field data from each of three orthogonal axes, determining best-fit parameters for an ellipsoid surface, calculating a transformation matrix that transforms the general ellipsoid surface into a spherical surface, applying the transformation matrix to the collected raw magnetic field data to determine calibrated magnetic field data values, and calculating a rotationally invariant magnitude of the magnetic field based on the calibrated magnetic field data values. In one embodiment, the step of determining the best-fit parameters for an ellipsoid surface comprises applying the equation: $Ax^2+By^2+Cz^2+2Dxy+2Exz+2Fyz+2Gx+2Hy+2Iz=1$. In another embodiment, the step of calculating a rotationally invariant magnitude of the magnetic field comprises applying the equation: $B=\sqrt{B_x^2+B_y^2+B_z^2}$, wherein B is the magnetic field.

Also described is a method of determining a directionality or directional line along which a target metal object lies. The method includes the steps of calibrating a magnetometer-based metal detection device to achieve rotational invariance, obtaining a positive detection of a magnetic field indicative of a target metal object via the magnetometer-based metal detection device, determining which axis of the three orthogonal axes is sensing an elevated magnetic field level above background, and equating the axis sensing an elevated magnetic field with the directionality or directional line along which the target metal object lies. In one embodiment, the method further includes the step of determining an absolute directionality or directional line, with respect to a horizontal plane, along which the target metal object lies via determination of acceleration vector direction of the at least one sensor. In another embodiment, the method further includes the step of determining the direction of maximum magnetic field magnitude with respect to the acceleration vector direction of the at least one sensor.

BRIEF DESCRIPTION OF THE DRAWINGS

FIG. 2, comprising FIG. 2A is a drawing of an exemplary magnetometer-based metal detection device. FIG. 2B is an image of another exemplary magnetometer-based metal detection device.

DETAILED DESCRIPTION

During surgical procedures, metallic objects can often be misplaced. Needles, for example, may be lost or misplaced within a human cavity. Because needles are small, they can be difficult to locate once misplaced. The present invention describes in part uniquely designed magnetometer-based metal detection devices and methods that can be used to precisely locate and determine the exact location and orientation of both magnetized and non-magnetized metal objects within a body cavity.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

As used herein, the term "substantially" means within 5% or 10% of the value referred to or within manufacturing tolerances.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Magnetometer-Based Metal Detection Devices

Figure 1:
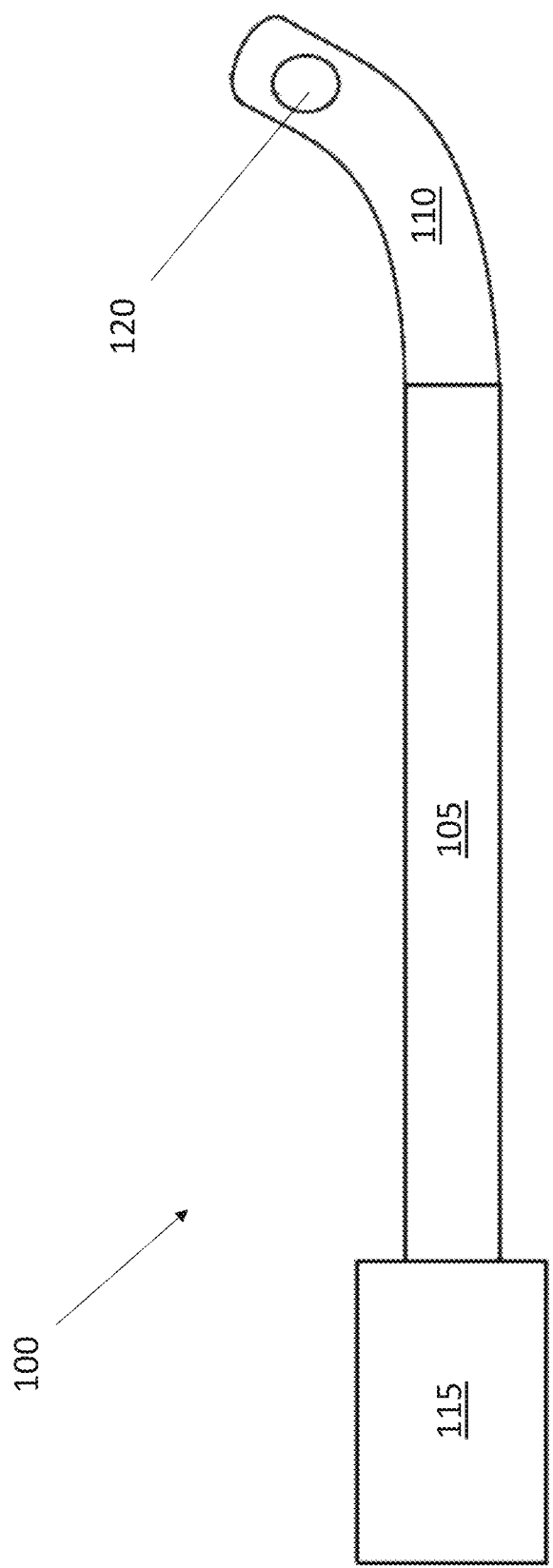
FIG. 1 is a schematic of an exemplary magnetometer-based metal detection device.
Figure 2A:
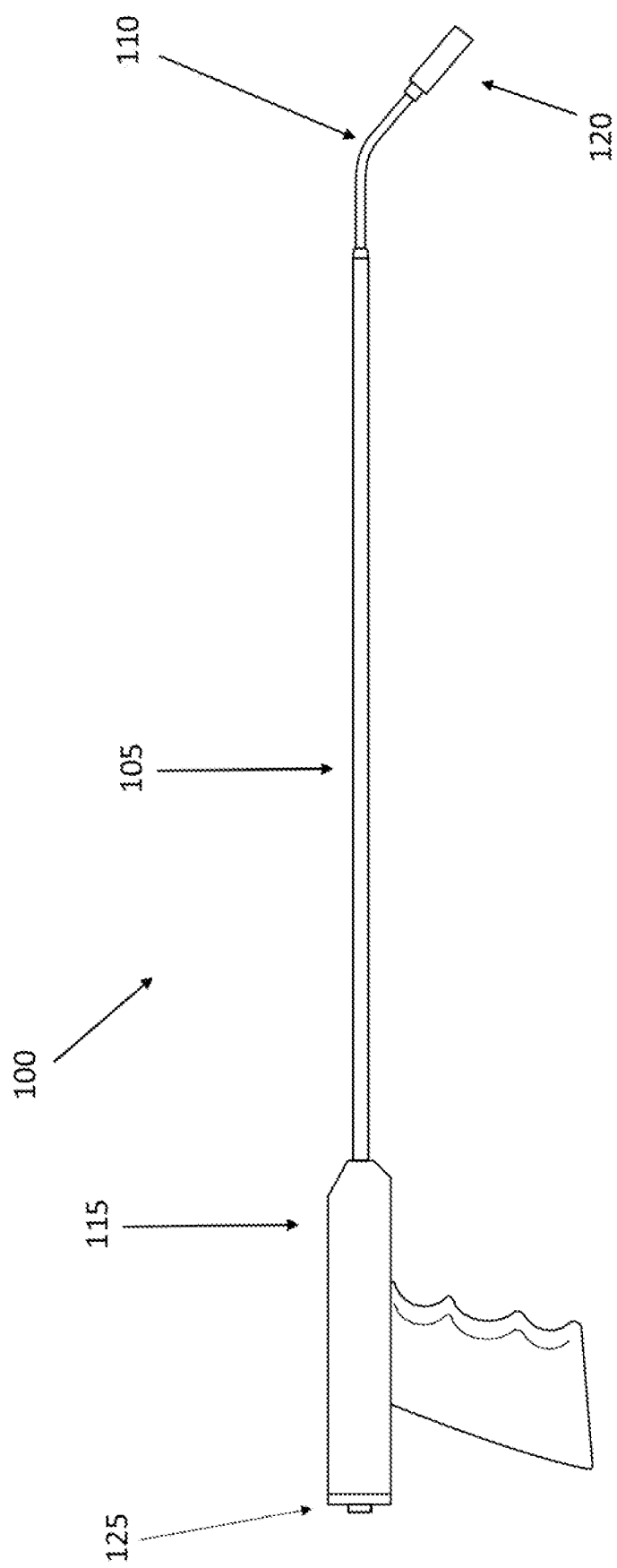
FIG. 2A and FIG. 2B, depicts an exemplary magnetometer-base metal detection device.
Figure 2B:
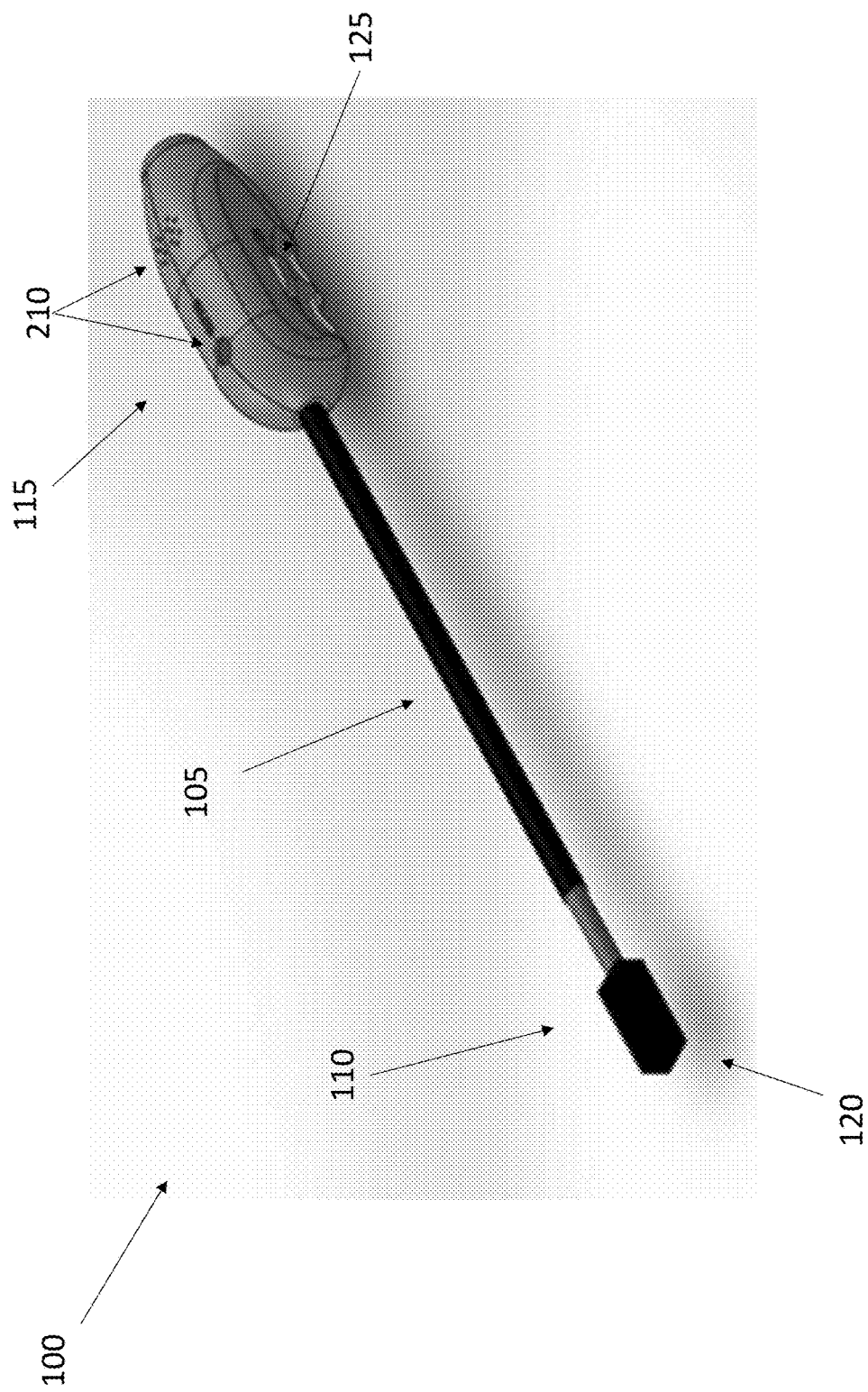

Referring now to FIGS. 1 and 2, a schematic (FIG. 1) and a photograph (FIG. 2) of an exemplary magnetometer-based surgical device 100 is shown. Device 100 may generally include an elongate central body 105, a distal portion 110, one or more magnetometers 120 positioned within distal portion 110, and a proximal portion 115 (such as a handle) for manipulating device 100 and the positioning of distal portion 110. Proximal portion 115, central body 105 and distal portion 110 of device 100 may be housed as a single unit, or as one or more separable components, as desired. In some embodiments, proximal portion 115, central body 105 and distal portion 110 form a sealed body. In other embodiments, central body 105 and distal portion 110 form a sealed body. It should be appreciated that there is no limitation to the actual size, shape or configuration of the housing and component portions of device 100. For example, device 100 may be designed for hand-held use by a physician, or it may be modified specifically for implementation via a robotic surgical system, such that proximal portion 115 integrates with or is easily graspable by a robotic arm from which central body 105, distal portion 110 and magnetometer(s) 120 can extend.

Also housed within device 100 may be one or more processors, memory, software, firmware or other programming logic, and any circuitry necessary to collect, process, transmit and display data from the one or more magnetometers 120 or other device 100 components. Device 100 may further include a power source, or an input for receiving power from an external power source. In some embodiments, device 100 may further include a user interface.

In some embodiments, for example as shown in FIG. 2, proximal portion 115 may include a handle for grasping device 100 by a physician. In other embodiments, for example a design of device 100 for use with a robotic surgical system, proximal portion 115 may be directly integrated into a robotic arm or grasper of the robotic surgical system. In other embodiments, proximal portion 115 may be sized and shaped for easy manipulation or engagement with a robotic grasper. In certain embodiments, proximal portion 115 may include one or more actuators or modulators 125 for adjusting or manipulating the position of distal portion 110 and/or any component associated therewith. For example, actuators 125 may be capable of activating, deactivating or adjusting sensitivity or output of one or more magnetometers 120, or any other component associated with distal portion 110. Such actuators 125 may be electrical or mechanical switches, buttons, levers, pulls, rods, grips, wheels, knobs, and the like that may engage or actuate any cables, wires or communication lines that pass through and permit mechanical and/or electrical communication between proximal portion 115 and distal portion 110 or any component associated therewith. In other embodiments, such communication between actuator 125 and component may be wireless. In still other embodiments, proximal portion 115 may include one or more motors to engage and promote movement of distal portion 110 via cables, rods, wires and the like. Proximal portion 115 may be constructed from any suitable material known in the art, for example plastic, polymer, rubber, metal, or a combination of materials. In certain embodiments, proximal portion 115 is constructed from non-metallic materials. In some embodiments, proximal portion 115 is constructed from surgically safe materials. In some embodiments, proximal portion 115 is constructed from biocompatible materials.

Central body 105 generally dictates the length of device 100, and may be any length desired. For example, as shown in FIG. 2, central body 105 may be a tubular member having a length of between 1 and 60 cm, including exemplary lengths of about 10, 20, 30, 40, 50 or 60 cm. Likewise, central body 105 may be any diameter desired. For example, central body 105 may have a diameter of between 2 and 20 mm, including exemplary diameters of about 5, 10, 15 or 20 mm. Central body 105 may be hollow or include at least one lumen suitable for any cables, rods, wires or communication lines to pass through central body 105 and permit mechanical and/or electrical communication between the proximal portion 115 and distal portion 110 of device 100. Central body 105 may be entirely rigid along its length, entirely flexible along its length, or contain one or more regions of flexibility along its length. Central body 105 may be constructed from any suitable material known in the art, for example plastic, polymer, rubber, metal, or a combination of materials. In certain embodiments, central body 105 is constructed from non-metallic materials. In some embodiments, central body 105 is constructed from surgically safe materials. In some embodiments, central body 105 is constructed from biocompatible materials.

Distal portion 110 may be the distal end region of central body 105, or it may be a separate component. In some embodiments, adjustable portion 110 includes a rounded distal end. In some embodiments, distal portion 110 may be rigid and in-line with a central axis running along the length of central body 105, or it may be rigid and angled outward or away from the central axis of central body 105. In other embodiments, distal portion 110 may be flexible and/or adjustable, such that distal portion 110 may adjustably extend, retract, or angle away from the central axis of central body 110. For example, in one embodiment, distal portion 110 may be connected to one or more cables, rods or wires (positioned internally or externally with respect to distal portion 110) that run through the lumen of central body 110 and engage one or more actuators 125 in proximal portion 115. Thus, by utilization of actuators 125, distal portion 110 may move in any direction, including extension or retraction, or angle radially away from the central axis of central body 105 in any desired direction. In some embodiments, distal portion 110 is oriented in line with the central axis of central body 105 when in a resting or disengaged position, such that actuation via actuators 125 causes movement of distal portion 110 that is out of line with the central axis of central body 105. In some embodiments, distal portion 110 is adjustable axially to an orientation of between 1° and 180° with respect to the central axis of central body 105. In other embodiments, distal portion 110 may include one or more motors to drive movement of distal portion 110 in any direction. In still other embodiments, distal portion 110 may include a preset curvature. For example, distal portion 110 may include a preset curvature that can be straightened when positioned within a straight lumen of central body 105. Then, when distal portion 110 is extended out of the lumen of distal portion 105, distal portion 110 returns to its curved, relaxed state. In some embodiments, adjustable portion 110 may include gooseneck tubing. Distal portion 110 may be constructed from any suitable material known in the art, for example plastic, polymer, rubber, metal or a combination of materials. In certain embodiments, proximal portion 115 is constructed from non-metallic materials. In some embodiments, proximal portion 115 is constructed from surgically safe materials. In some embodiments, proximal portion 115 is constructed from biocompatible materials.

Each magnetometer 120 generally includes at least one sensor or sensing element capable of detecting and/or measuring the magnitude and/or direction of a magnetic field. Any type of sensor or sensing element may be used, and any type of magnetometer may be used, as would be understood by those skilled in the art. Magnetometer 120, for example, may be a vector magnetometer that can measure the vector components of a magnetic field. Magnetometer 120, as another example, may include a total field magnetometer or a scalar magnetometer that can measure the magnitude of the vector magnetic field. In some embodiments, magnetometer 120 may include a Hall Effect magnetometer or a Hall Effect sensor. In some embodiments, magnetometer 120 may include a magneto-resistive device. Magnetometer 120, for example, may include thin strips of permalloy (e.g., NiFe magnetic film) whose electrical resistance varies with a change in magnetic field. In other embodiments, magnetometer 120 may include an inductive sensor. In some embodiments, magnetometer 120 may include a magneto-resistive device that provides a change in resistance in response to a change in a magnetic field along a given axis. In some embodiments, magnetometer 120 may include an anisotropic magneto-resistive material.

In one embodiment, device 100 includes at least one single-axis magnetometer 120. In another embodiment, device 100 includes at least two magnetometers 120 where the axis of each magnetometer 120 is 90° from each other. In another embodiment, device 100 includes at least three magnetometers 120 where the axis of each magnetometer 120 is 90° from each other. In yet another embodiment, magnetometer 120 is a three-axis magnetometer, where each axis is 90° from each other, for example a 3-axis magneto-resistive (AMR) sensor.

In some embodiments, magnetometer 120 may include a communication interface that may provide magnetic field data using a communication protocol. The communication interface, for example, may include an I²C digital interface. In some embodiments, the communication interface may include a micro-controller or microprocessor interface.

In some embodiments, magnetometer 120 may be packaged in a single application-specific integrated circuit (ASIC) package. In some embodiments and without limitation, magnetometer 120 may have a package size less than 2.5, 5, 7.5, 10, 12.5, 15, etc. cubic millimeters. In some embodiments, magnetometer 120 includes a surface mount package. In some embodiments, a 3-axis magneto-resistive sensor is a magnetic sensor including an ultra-high-power high performance three-axis magnetic sensor. In some embodiments, magnetometer 120 may be packaged in a land grid array package (LGA).

In some embodiments, magnetometer 120 may include an analog to digital converter (ADC) such as, for example, a 12-Bit ADC. In some embodiments, magnetometer 120 may include a low noise AMR sensor. In some embodiments and without limitation, magnetometer 120 may have a field resolution of about ±4 Gauss, about ±8 Gauss, about ±12 Gauss, or about ±16 Gauss Fields. In some embodiments, magnetometer 120 may include a self-test or self-calibration.

In some embodiments and without limitation, magnetometer 120 may operate with a low voltage power supply such as, for example, a power supply providing voltage less than about 2.0 V, 2.5 V, 3.0 V, 3.5 V, 4.0 V, 4.5 V, 5.0 V, 5.5 V, 6.0 V, etc. and/or may have low power consumption such as, for example, current consumption of less than about 50 µA, 75 µA, 100 µA, 125 µA, 150 µA, 175 µA, 200 µA, 1000 µA, etc. In some embodiments, magnetometer 120 may provide data at an output of greater than 50 Hz, 100 Hz, 150 Hz, 200 Hz, 250 Hz, 300 Hz, etc.

Figure 3:
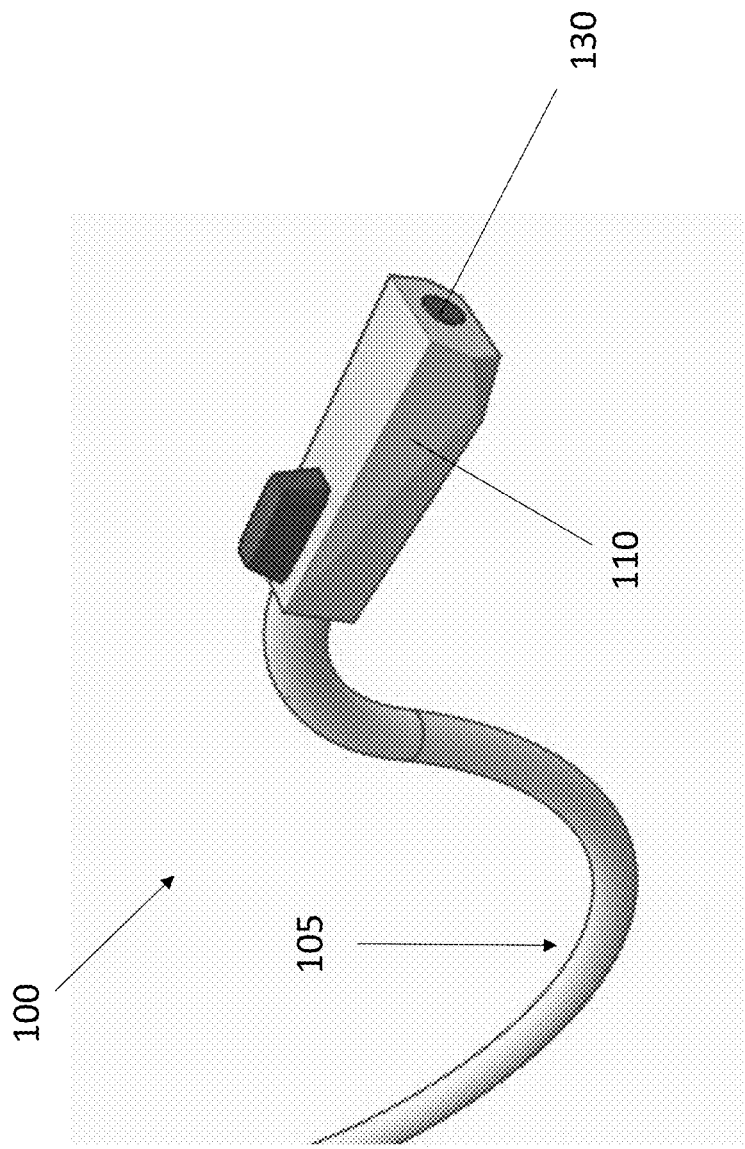
FIG. 3 is a schematic of an exemplary magnetometer-based metal detection device suitable for use with a robotic surgical system.

Device 100 may further include other functional components, particularly within distal portion 110. For example, distal portion 110 may further include an accelerometer, gyroscope, light sensor, pressure sensor, or voltage sensor. In another embodiment, distal portion 110 may further include one or more permanent magnets and/or one or more electromagnets 130, as shown in FIG. 3. For example, device 100 may include an electromagnet disposed at the distal end of distal portion 110. When a user is searching or scanning for a magnetic object the electromagnet may be turned off. When the user has located the magnetic object, the user may turn on the electromagnet, and the electromagnet may magnetically engage with the magnetic object. In some embodiments, the electromagnet has a variable field strength. In some embodiments, the field strength is adjustable between one or more strength levels. In some embodiments, the field strength may be adjusted between high strength and low strength.

Figure 4:
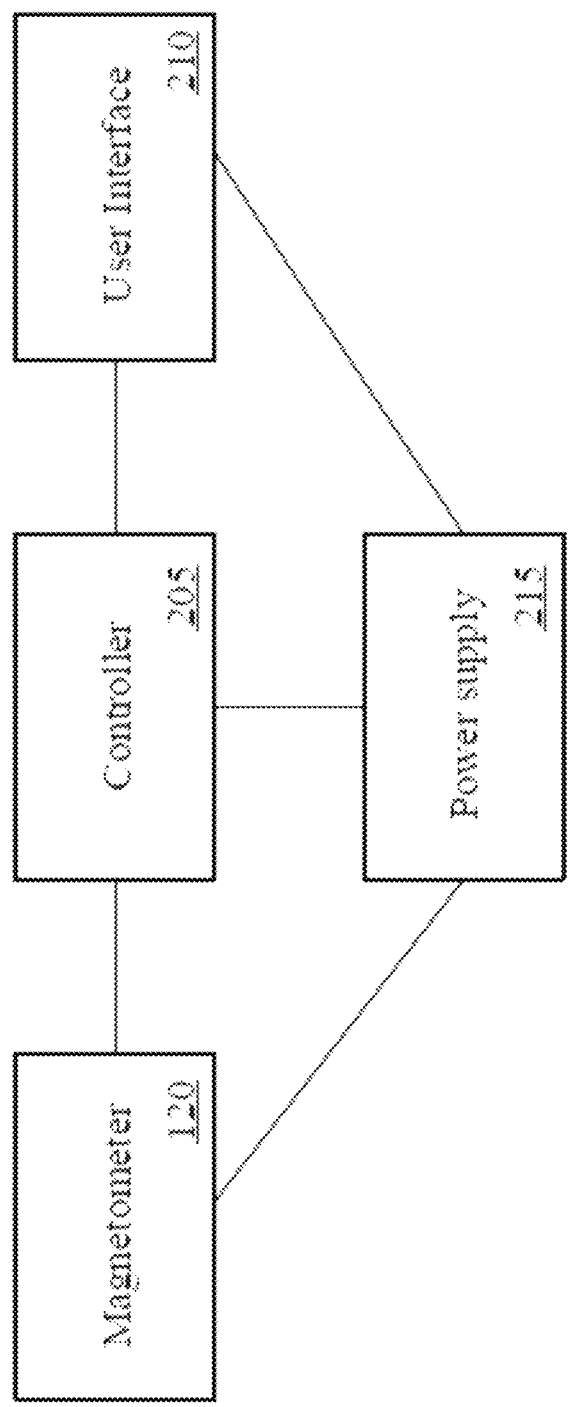
FIG. 4 is a block diagram of an exemplary electrical system of a magnetometer-based metal detection device.

Referring now to FIG. 4, a block diagram illustrating an exemplary electrical system 200 of device 100 is shown. In some embodiments, electrical system 200 includes one or more magnetometers 120, at least one controller 205, at least one user interface 210, and/or a power supply 215. In some embodiments, controller 205 communicatively couples with magnetometer 120, user interface 210, and/or power supply 215 such as, for example via a bus or via a direct communication path.

Figure 5:
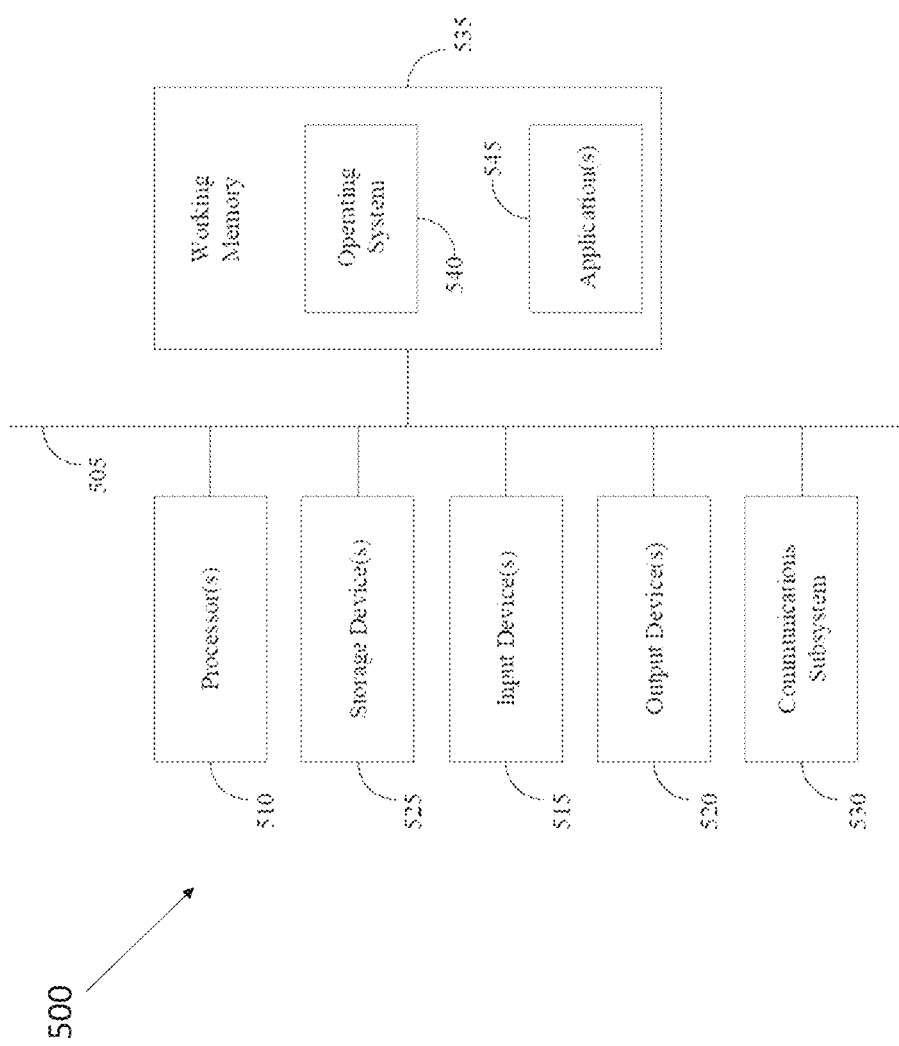
FIG. 5 is a block diagram of an exemplary computational system of a magnetometer-based metal detection device.

In some embodiments, one or more controllers 205 may be any type of processor, microprocessor or computer such as, for example, all or portions of computational system 500 shown in FIG. 5. In some embodiments, controller 205 includes processing logic such as, for example, to control the operation of one or more of user interface 210, magnetometer 120 and/or any other functional components (such as an accelerometer or electromagnet) associated with device 100. In some embodiments, controller 205 may receive data from one or more magnetometers 120. The data received from magnetometer 120, for example, may include voltage values that correspond to or are indicative of the magnetic field strength near magnetometer 120. Controller 205, for example, may include or be coupled with an analog to digital converter that converts the voltage values to digital values that may be processed by controller 205. In some embodiments, data received from magnetometer 120, may include digital data that include values that correspond with the magnetic field strength near magnetometer 120. In some embodiments, the data provided by magnetometer 120 may be received at controller 205 in any format.

In some embodiments, user interface 210 may include buttons, dials, switches, displays, touch screens, input devices, lights, speakers, or any other component suitable for interaction and/or interpretation by a user. User interface 210 may be a single component or multiple components, and may be positioned anywhere on or along device 100 as desired. For example, one or more components of user interface 210 may be positioned on proximal portion 115, on central body 105, or on distal portion 110. One or more components of user interface 210 may also be positioned externally or separately from device 100, such that device 100 effectively forms part of a larger system optionally including device 100, external computing and communication components, at least a portion of user interface 210, and a power source. The output of user interface 210 may depend on the magnetic field measurements received at controller 205. In some embodiments, controller 205 may control the output of the user interface 210 based on data received from the magnetometer 120. As another example, controller 205 may control operation of the magnetometer such as, for example, the measurement mode of the magnetometer 120, based on input from the user interface 210. In some embodiments, user interface 210 includes visual indicators corresponding to various values or strengths of a detected magnetic field, such as a plurality of indicator lights (for example light emitting diodes (LEDs)). In some embodiments, controller 205 instructs user interface 210 to turn on a first light of the plurality of lights when the magnetic field measured with magnetometer 120 is greater than a first threshold value or baseline value. In some embodiments, controller 205 instructs user interface 210 to turn on a second light of the plurality of lights when the magnetic field measured with the magnetometer 120 is greater than a second threshold value. In some embodiments, controller 205 instructs user interface 210 to turn on a third light of the plurality of lights when the magnetic field measured with magnetometer 120 is greater than a third threshold value. In some embodiments, controller 205 instructs user interface 210 to continue to turn on lights as the magnetic field measured by magnetometer 120 increases. Alternatively or additionally, controller 205 may instruct user interface 210 to turn off lights as the magnetic field measured by magnetometer 120 decreases. As such, the user may view the user interface and determine whether device 100 is moving away from or toward areas of greater or lesser magnetic field strength.

In some embodiments, user interface 210 may include a sound emitting device, for example a speaker, for transmission of audio indicators corresponding to various values or strengths of a detected magnetic field. In some embodiments, controller 205 instructs user interface 210 to produce a first tone with a first frequency or first amplitude when the magnetic field measured with magnetometer 120 is greater than a first threshold. Similarly, controller 205 may instruct user interface 210 to produce a second tone with a second frequency or second amplitude when the magnetic field measured with the magnetometer 120 is greater than a second threshold. Controller 205 may instruct user interface 210 to produce a third tone with a third frequency or third amplitude when the magnetic field measured with magnetometer 120 is greater than a third threshold. Controller 205 may instruct user interface 210 to continue to change the tone by changing the amplitude and/or frequency of the tone as the magnetic field measured by magnetometer 120 increases. Alternatively or additionally, controller 205 may instruct user interface 210 to continue to change the tone by changing the amplitude and/or frequency of the tone as the magnetic field measured by magnetometer 120 decreases. Accordingly, the user may listen to the user interface and determine whether magnetometer surgical device 100 is moving in a direction away from or toward areas with greater or lesser magnetic field strength.

In some embodiments, user interface 210 may include a visual display that receives instructions from controller 205 that may display magnetic field strength in other formats, such as text, numerical values, bar graphs depicting increasing or decreasing magnitude of the magnetic field strength, graphics related to the magnetic field strength, the direction of greater magnetic field strength, or other means of visually depicting such values.

In some embodiments and without limitation, power supply 215 includes one or more batteries, one or more rechargeable batteries, an electrical cord that may be connected to the power grid, a DC power supply, an AC power supply, or the like.

It should also be appreciated that all of electrical system 200 may be housed within device 100, or alternatively only a portion of electrical system 200 is housed within device 100. In one embodiment, at least a portion of user interface 210 is external and separate from device 100. For example, a visual display, such as a computing monitor, may be communicatively connected to device 100 but physically separate from device 100. In another embodiment, power supply 215 may be an external power supply that device 100 is capable of plugging into and drawing power from.

Referring now to FIG. 5, computational system 500 (or processing unit) is illustrated that can be used to perform and/or control operation of any of the device and system embodiments described herein. For example, computational system 500 can be used alone or in conjunction with other computing components or sensory components. As another example, computational system 500 can be used to perform any calculation, solve any equation, perform any identification, and/or make any determination described herein.

In some embodiments, computational system 500 may include any or all of the hardware elements contemplated herein. In some embodiments, computational system 500 may include hardware elements that can be electrically coupled via a bus 505 (or may otherwise be in communication, as appropriate). The hardware elements can include one or more processors 510, including, without limitation, one or more general-purpose processors and/or one or more special-purpose processors (such as digital signal processing chips, graphics acceleration chips, and/or the like); one or more input devices 515, which can include, without limitation, a mouse, a keyboard, and/or the like; and one or more output devices 520, which can include, without limitation, a display device, a printer, and/or the like.

In some embodiments, computational system 500 may further include (and/or be in communication with) one or more storage devices 525, which can include, without limitation, local and/or network-accessible storage and/or can include, without limitation, a disk drive, a drive array, an optical storage device, a solid-state storage device, such as random access memory ("RAM") and/or read-only memory ("ROM"), which can be programmable, flash-updateable, and/or the like. In some embodiments, computational system 500 includes a communications subsystem 530, which can include, without limitation, a modem, a network card (wireless or wired), an infrared communication device, a wireless communication device, and/or chipset (such as a Bluetooth® device, an 802.6 device, a WiFi device, a WiMAX device, cellular communication facilities, etc.), and/or the like. Communications subsystem 530 may permit data to be exchanged with a network (such as the network described below, to name one example) and/or any other devices described herein. In some embodiments, computational system 500 will further include a working memory 535, which can include a RAM or ROM device, as described above.

In some embodiments, computational system 500 also includes software elements, shown as being currently located within working memory 535, including an operating system 540 and/or other code, such as one or more application programs 545, which may include computer programs of the invention, and/or may be designed to implement methods of the invention and/or configure systems of the invention, as described herein. For example, one or more procedures described with respect to the method(s) contemplated herein may be implemented as code and/or instructions executable by a computer (and/or a processor within a computer). A set of these instructions and/or codes may be stored on a computer-readable storage medium, such as storage device(s) 525 described above.

In some embodiments, the storage medium may be incorporated within computational system 500 or in communication with computational system 500. In other embodiments, the storage medium may be separate from computational system 500 (e.g., a removable medium, such as a compact disc, etc.), and/or provided in an installation package, such that the storage medium can be used to program a general-purpose computer with the instructions/code stored thereon. These instructions might take the form of executable code, which is executable by computational system 500 and/or might take the form of source and/or installable code, which, upon compilation and/or installation on computational system 500 (e.g., using any of a variety of generally available compilers, installation programs, compression/decompression utilities, etc.), then takes the form of executable code.

Methods

The magnetometer-based metal detection devices as described herein may be used to identify and/or locate the presence of a metal object in the body of a patient during a surgical procedure, and in some embodiments, may be further used to remove such metal objects or to assist with the removal of such metal objects. In some embodiments, the metal objects are magnetic. In some embodiments, the metal objects are not magnetic. In some embodiments, metal objects may be magnetized prior to use in a surgical procedure. In some embodiments, metal objects may be magnetized during the surgical procedure, or in situ.

Figure 6:
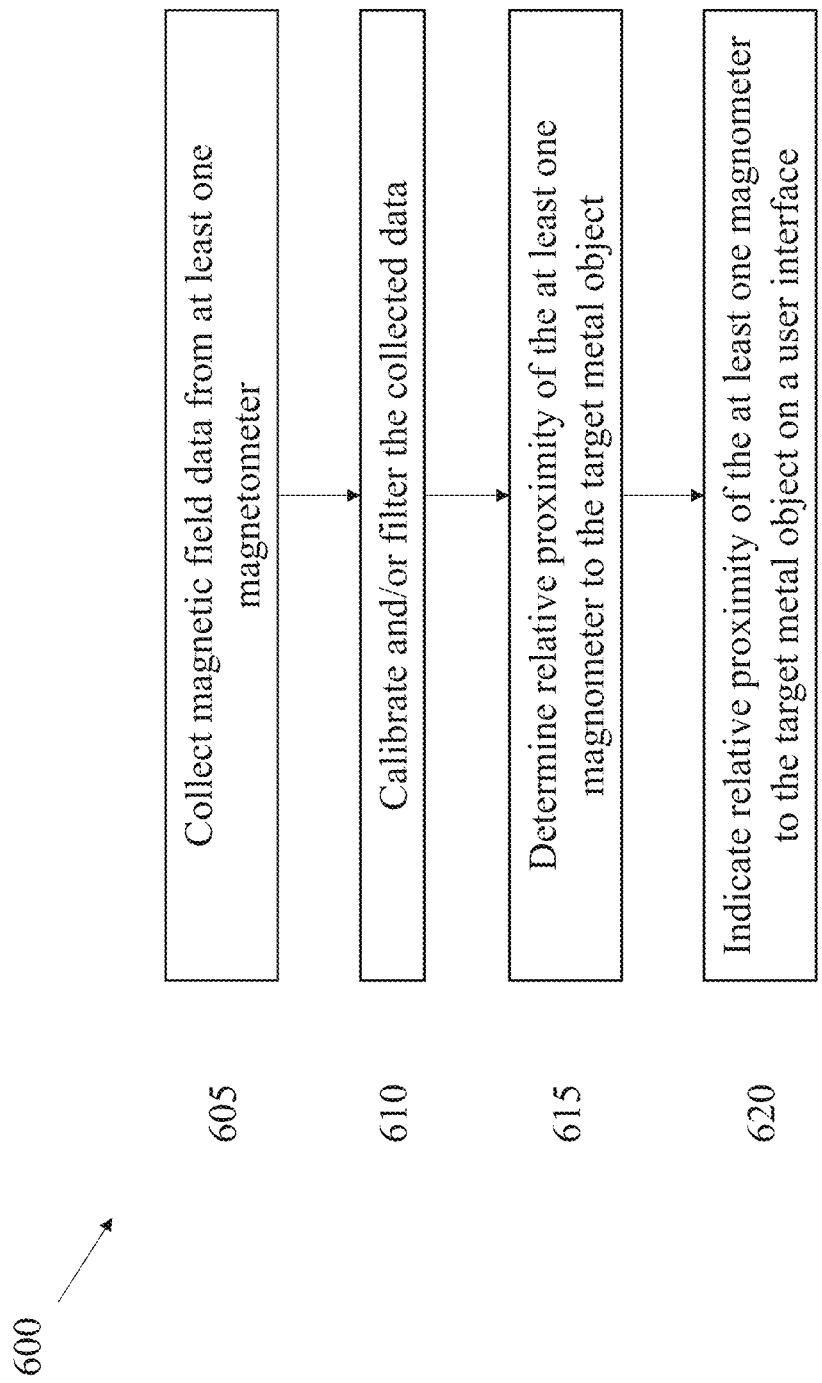
FIG. 6 is a flow chart of an exemplary process for determining the presence of a target metal object in a surgical procedure.

Referring now to FIG. 6, an example process 600 for determining the presence of metal object in a surgical procedure is shown. One or more steps of process 600 may be implemented, in some embodiments, by one or more components of the magnetometer-based metal detection devices and systems described herein. Although process 600 is illustrated as discrete blocks, various blocks may be divided into additional blocks, combined into fewer blocks, or eliminated, depending on the desired implementation.

In some embodiments, process 600 begins at block 605. At block 605 magnetic field data is received by a controller from one or more magnetometers. The magnetic field data may include, for example, analog voltage values that correspond to the magnetic field strength near the magnetometer and/or digital values that correspond to the magnetic field strength near the magnetometer.

In some embodiments, at block 610 the magnetic field data may be calibrated or filtered. For example, background noise (background magnetic fields) may be filtered from the magnetic field data using any of the calibrating or filtering methods described herein, or any other calibrating or filtering algorithm or technique understood by those skilled in the art. In one embodiment, the Earth's magnetic field may be filtered from the magnetic field data. The magnetic field data may include, for example, data that includes both amplitude and direction of the magnetic field such as, for example, from a 3-axis magnetometer. The Earth's magnetic field may be determined by tracking the Earth's magnetic field data over time and removed through one or more filtering algorithms. Alternatively, or additionally, the magnitude and direction of the Earth's magnetic field may be determined based on an average of the magnetic field data prior to searching for a metal object such as, for example, during a calibration procedure and/or while a user selects a calibration procedure through a user interface of the device or system.

In some embodiments, at block 615 the relative proximity of the distal end of the magnetometer-based metal detection device and/or the magnetometer may be determined from the magnetic field data. For example, the controller may calculate a moving average of the magnetic field data. The moving average of the magnetic field data can then be compared with a threshold value. If the moving average of the magnetic field data is greater than a threshold value, then the magnetometer or distal end of the device may be within a specific distance from the metal object. The moving average, for example, may be compared with one or more threshold values that each correspond with a different relative proximity of the magnetometer or distal end of the device with the metal object.

In some embodiments, at block 620 the controller may provide a signal to the user interface to indicate the proximity of the magnetometer or distal end of the device relative to the metal object. For example, the user interface may provide and/or change an audible sound in response to a change in the relative proximity of the magnetometer or distal end of the device relative to the metal object. As another example, the user interface may provide and/or change the illumination of one or more lights in response to a change in the relative proximity of the magnetometer or distal end of the device relative to the metal object. As another example, the user interface may provide and/or change the graphics or text on a display in response to a change in the relative proximity of the magnetometer or distal end of the device relative to the metal object.

In some embodiments, process 600 may be repeated as the user manipulates the magnetometer-based metal detection device during a surgical procedure.

Figure 7:
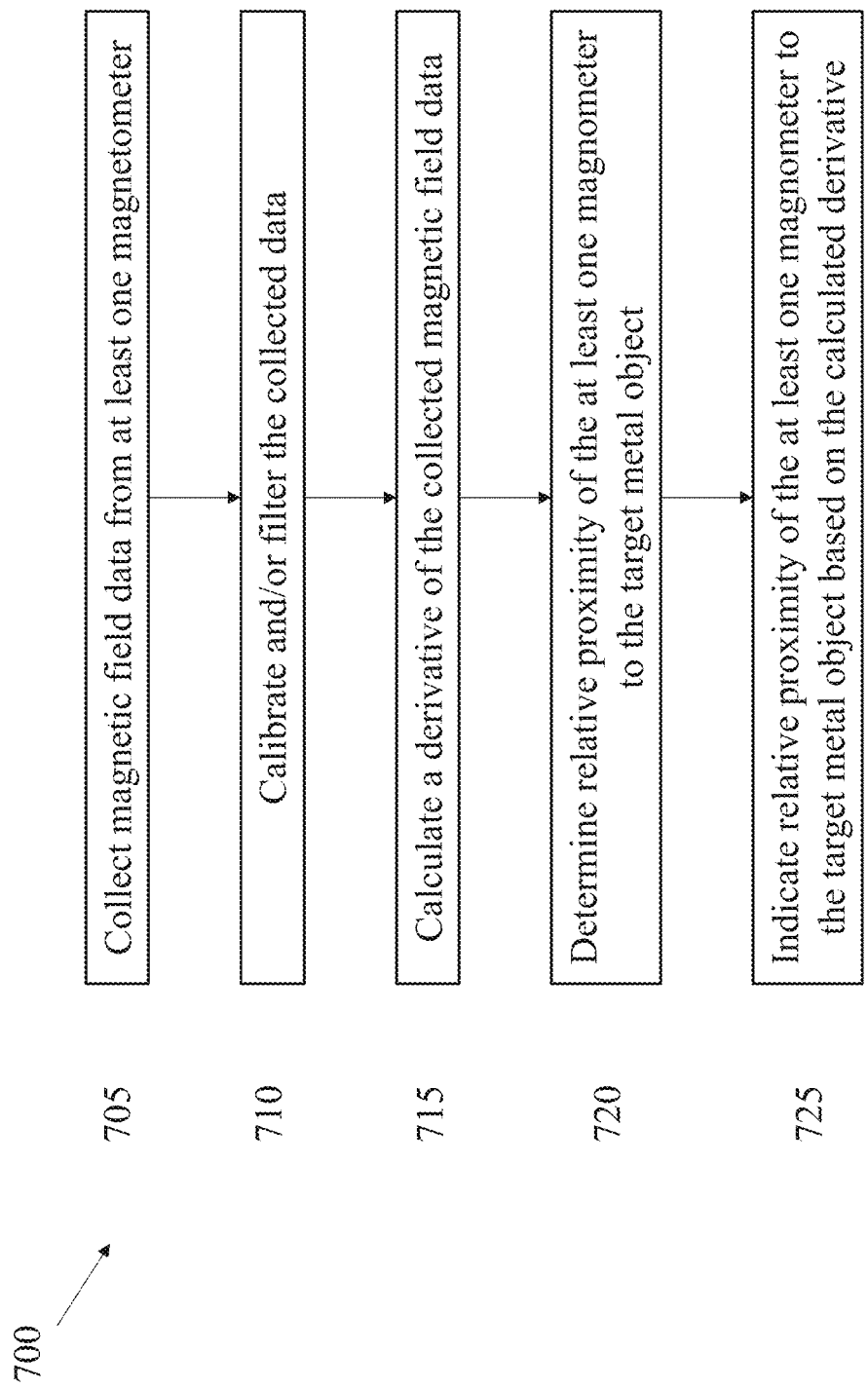
FIG. 7 is a flow chart of another exemplary process for determining the presence of a target metal object in a surgical procedure.

Referring now to FIG. 7, a flowchart of an example process 700 for determining the presence of a metal object in a surgical procedure, according to some embodiments is depicted. One or more steps of process 700 may be implemented, in some embodiments, by the magnetometer-based metal detection devices and systems described herein. Although process 700 is illustrated as discrete blocks, various blocks may be divided into additional blocks, combined into fewer blocks, or eliminated, depending on the desired implementation.

In some embodiments, process 700 begins at block 705. Within block 705 magnetic field data is received by the controller from the magnetometer. The magnetic field data may include, for example, analog voltage values that correspond to the magnetic field strength near the magnetometer or distal end of the device, and/or digital values that correspond to the magnetic field strength near the magnetometer or distal end of the device.

In some embodiments, at block 710 the magnetic field data may be calibrated or filtered. For example, background noise (background magnetic fields) may be filtered from the magnetic field data using any of the calibrating or filtering methods described herein, or any other calibrating or filtering algorithm or technique understood by those skilled in the art. In one embodiment, the Earth's magnetic field may be filtered from the magnetic field data. The magnetic field data may include, for example, data that includes both amplitude and direction of the magnetic field such as, for example, from a 3-axis magnetometer. The Earth's magnetic field may be determined by tracking the Earth's magnetic field data over time and removed through one or more filtering algorithms. Alternatively or additionally, the magnitude and direction of the Earth's magnetic field may be determined based on an average of the magnetic field data prior to searching for a metal object such as, for example, during a calibration procedure and/or while a user selects a calibration procedure through a user interface of the device or system.

In some embodiments, at block 715 a derivative of the magnetic field data may be calculated. This may be accomplished using any number of algorithms or mathematical tools understood by those skilled in the art. For example, the derivative can understood as the difference between successive data points, which for data points 1 and 2 could be expressed as:

$$\frac{\Delta B}{\Delta t} = B_2 - B_1 \qquad \text{Equation 1}$$

Where B is the magnetic field strength, t is time, $\Delta B/\Delta t$ is the change in the magnetic field with respect to an incremental change in time, $B_1$ is the magnetic field strength at a particular time interval, and $B_2$ is the magnetic field strength at a later time interval.

This calculation can be repeated continuously and used to determine whether the magnetic field was increasing or decreasing, or whether a peak in magnetic field was measured (these processes are carried out in block 720 and 725 as described below).

In some embodiments, at block 720 the controller can be used to determine whether the magnetometer is getting nearer or farther from the metal object based on the derivative data. For example, a local maximum of the derivative of the magnetic field data can indicate that the magnetic field strength is increasing or decreasing thus indicating that the sensor is moving toward or away from the target, respectively. A local maximum is positively identified when the derivative change from a positive value to a negative value.

In some embodiments, at block 725 the controller may provide a signal to the user interface to indicate whether the device is getting nearer or farther from the metal object. In some embodiments, the user interface may provide and/or change an audible sound in response to a change in the derivative of the magnetic field data. In some embodiments, the user interface may provide and/or change the illumination of one or more lights in response to a change in the derivative of the magnetic field data. In some embodiments, the user interface may provide and/or change the graphics or text on a display in response to a change in the derivative of the magnetic field data.

Process 700 may be repeated as the user manipulates the magnetometer-based metal detection device during a surgical procedure.

In some embodiments, the magnetometer-based metal detection device may switch between different detection modes such as, for example, in response to a user flipping a switch, for example a switch on the handle or on the controller, or selecting a button on the magnetometer-based metal detection device. In a first mode, for example, the magnetometer-based metal detection device may execute process 600. In the first mode, for example, a user may operate the magnetometer-based metal detection device to determine whether any metal object is found within a body during a surgical procedure.

Using the second mode, for example, the magnetometer-based metal detection device may execute process 700. In the second mode, for example, a user may operate the magnetometer-based metal detection device to determine the location of any metal object found within a human body by following the path of increasing magnetic field data with the magnetometer-based metal detection device.

Figure 8:
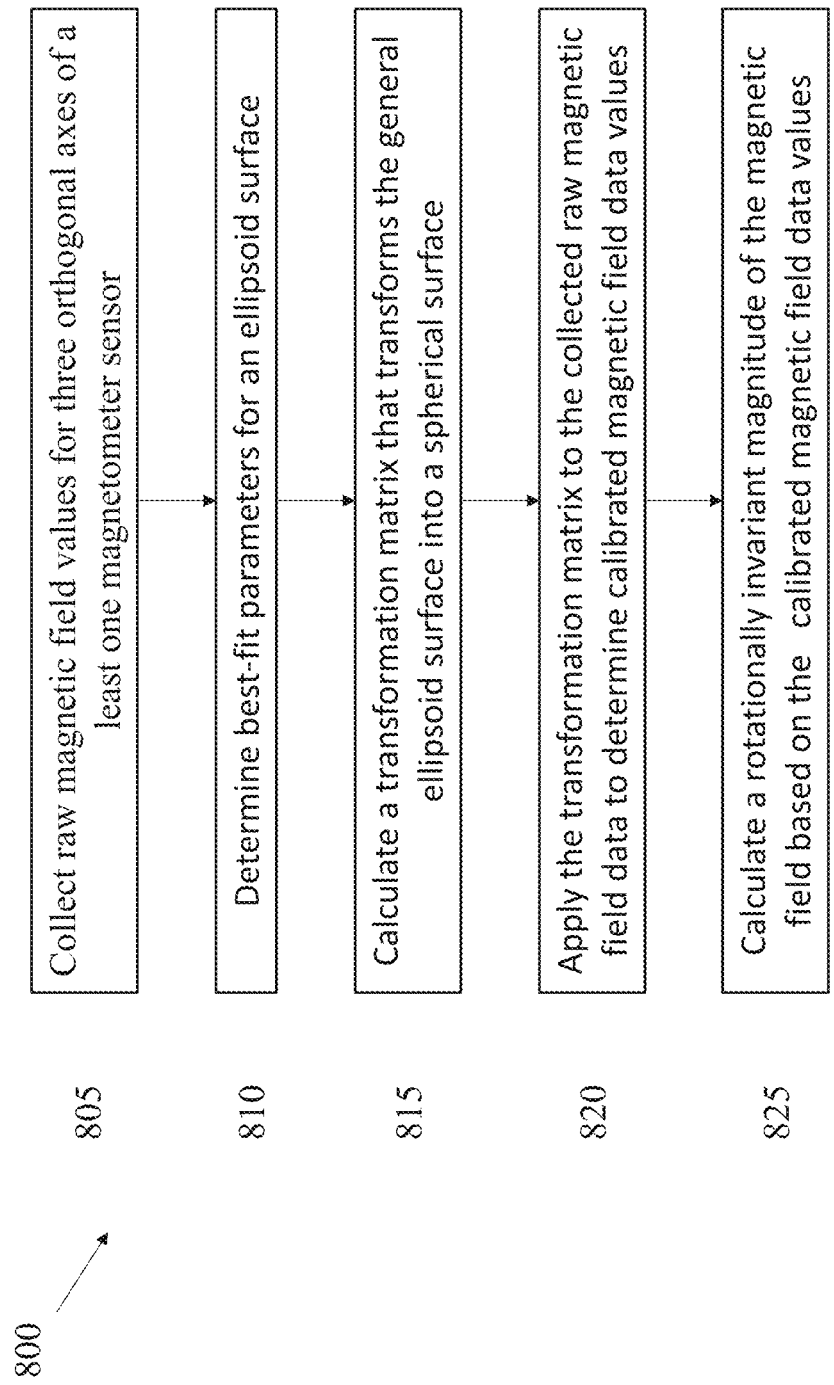
FIG. 8 is a flow chart of an exemplary process for calibrating a magnetometer-based metal detection device for rotational invariance.
Figure 9:
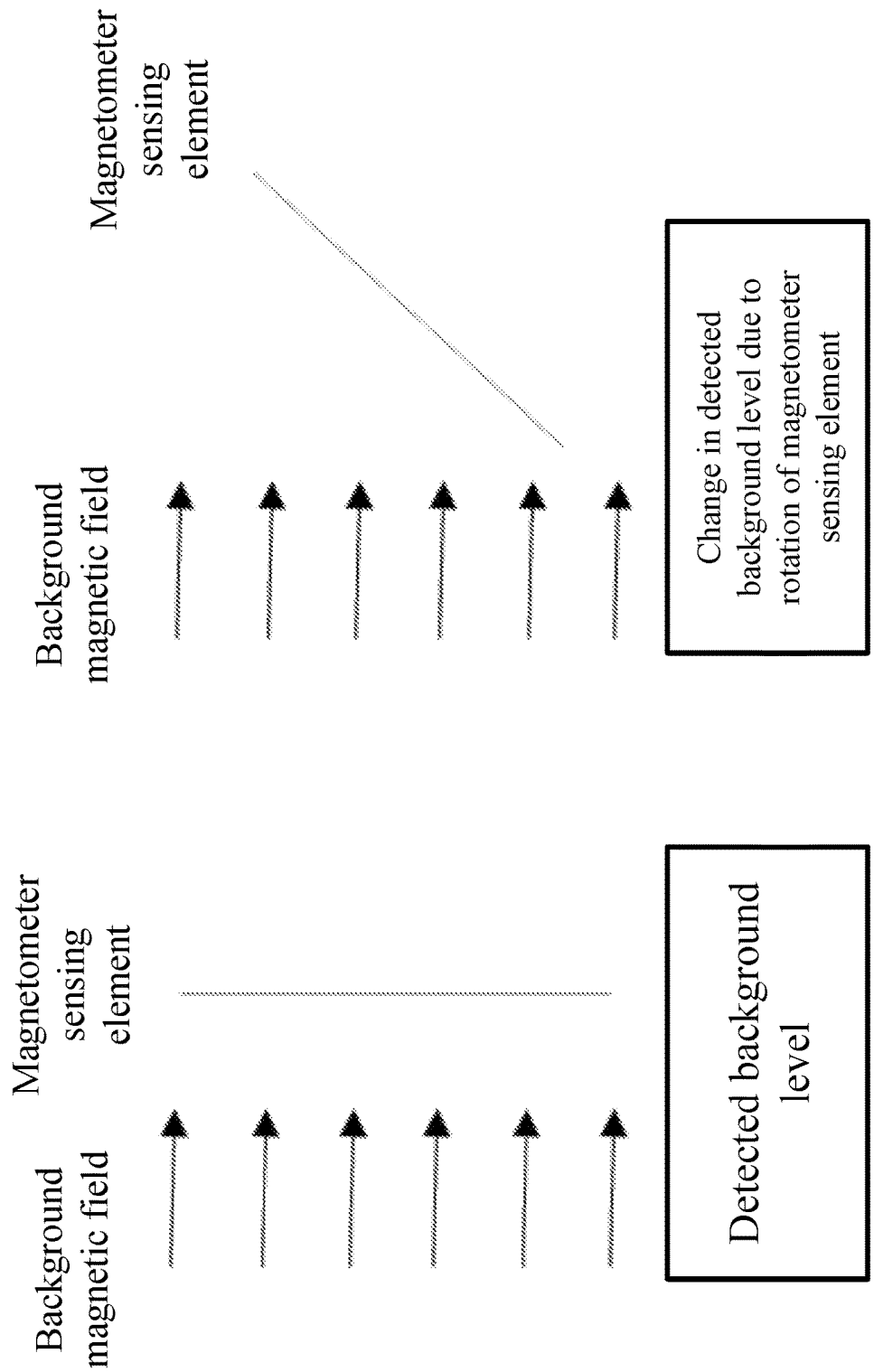
FIG. 9 is a diagrammatic representation of two sensing elements relative to a magnetic field.

Referring now to FIG. 8, a flow chart of an exemplary process 800 is shown for calibrating the magnetometer-based metal detection device to compensate for rotational artifacts that may occur during standard operation of the magnetometer-based metal detection device in order to achieve rotational invariance. Because the body of a patient is typically not moveable during a surgical procedure, fixing the location of the magnetometer sensor(s) is not possible when searching for a lost needle in a patient using a mobile tool, because the tool must be moved in order to search the stationary body cavity. Accordingly, the detected background magnetic field changes as the sensor(s) moves. Of particular concern is the fact that rotation of the magnetometer sensor(s) causes large changes in detected background because the magnetic detection is based on the amount of field passing through a planar sensing element, as depicted in FIG. 9. Accordingly, it was the unexpected finding that successful implementation of a mobile metal detection device capable of detecting small metal objects, such as needles, is achieved or significantly improved by removal of rotational variation from background magnetic field data. In one embodiment, process 800 may be used to simultaneously measure the magnetic field in three orthogonal directions and calibrating these values by fitting them onto a spherical surface. This calibration process rescales the raw values on the three axes to a common scale and remove any offsets. The calibrated values are then suitable for use by the magnetometer-based metal detection device software or firmware to provide a calculation of the magnitude of the local magnetic field that is invariant under rotation of the device.

One or more steps of process 800 may be implemented, in some embodiments, by the magnetometer-based metal detection devices and systems described herein. Although process 800 is illustrated as discrete blocks, various blocks may be divided into additional blocks, combined into fewer blocks, or eliminated, depending on the desired implementation.

In some embodiments, at block 805 raw magnetic field data is received by the controller from each axis of a three-axis magnetometer, or from each axis of three magnetometers, where the axis of each magnetometer is orthogonal or 90° from each other. The raw magnetic field data may include, for example, analog voltage values that correspond to the magnetic field strength near the magnetometer(s) or distal end of the device, and/or digital values that correspond to the magnetic field strength near the magnetometer(s) or distal end of the device.

In some embodiments, at block 810, a fitting algorithm is implemented by the controller in order to determine the best-fit parameters for an ellipsoid. In some embodiments, Equation 2 is used to determine the best-fit parameters.

$$Ax^2+By^2+Cz^2+2Dxy+2Exz+2Fyz+2Gx+2Hy+2Iz=1 \qquad \text{Equation 2}$$

In some embodiments, at block 815 a calculation is performed to determine the transformation matrix that transforms the general ellipsoid surface computed at block 510 into a spherical surface centered at the origin.

In some embodiments, at block 820, the transformation matrix calculated in block 815 is applied to all new raw values collected in block 805 in order to obtain calibrated values.

In some embodiments, at block 825, the calibrated values calculated at block 820 are used to calculate the rotationally invariant magnitude of the magnetic field, B, as shown in Equation 3.

$$B=\sqrt{B_x^2+B_y^2+B_z^2} \qquad \text{Equation 3}$$

In some embodiments, the angle $\theta$ between the vertical z axis and the x-y plane of the sensor is calculated as shown in Equation 4:

$$\theta = cos^{-1}\left(\frac{B_z}{B}\right) \qquad \text{Equation 4}$$

In some embodiments, the angle $\Phi$ between the x-axis and the x-y plane of the sensor is calculated as shown in Equation 5:

$$\varphi = tan^{-1}\left(\frac{B_y}{B_x}\right) \quad \text{Equation 5}$$

Figure 10:
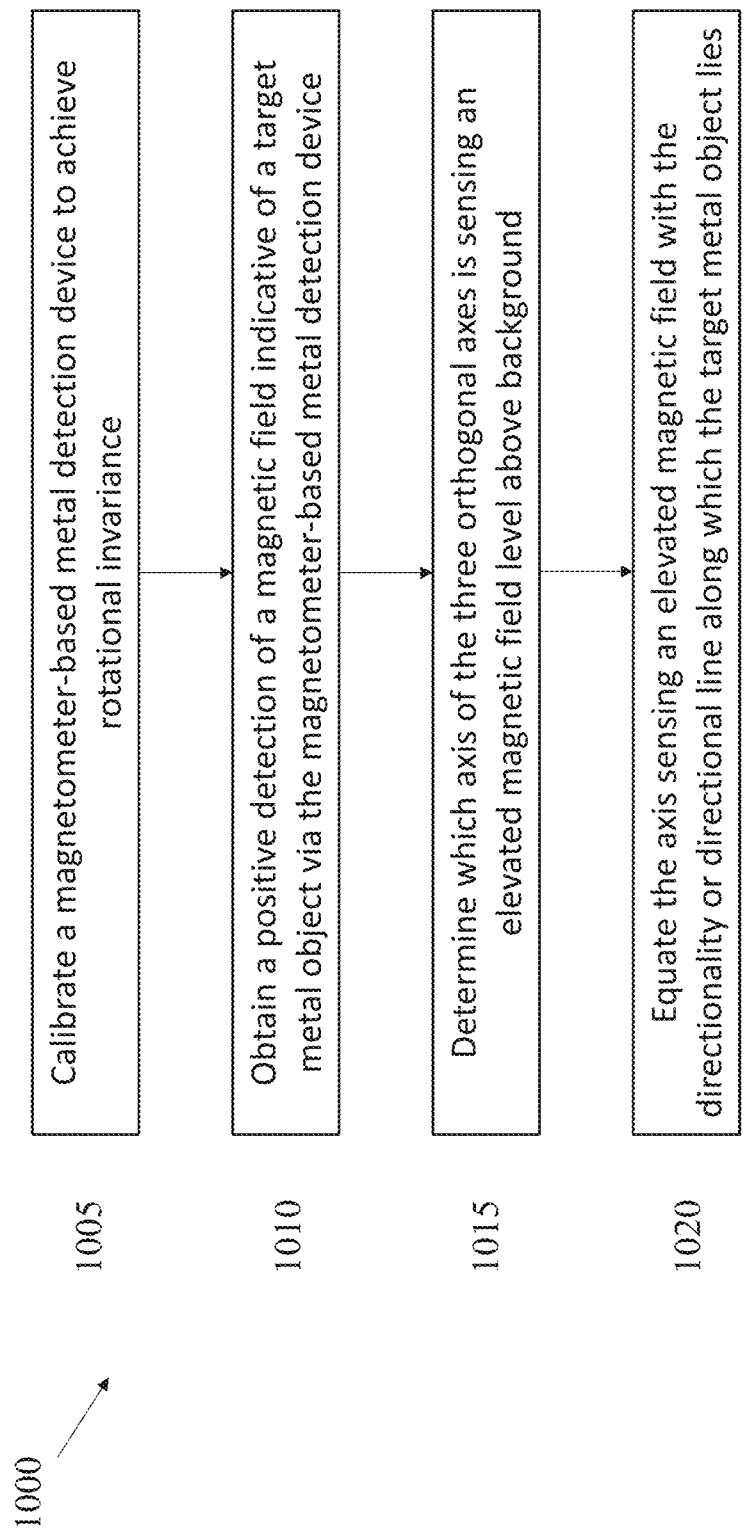
FIG. 10 is a flow chart of an exemplary process for determining the directionality or directional line along which a target metal object lies.

Referring now to FIG. 10, a flowchart of an example process 1000 for determining the directionality or directional line along which the target metal object lies.

One or more steps of process 1000 may be implemented, in some embodiments, by the magnetometer-based metal detection devices and systems described herein. Although process 1000 is illustrated as discrete blocks, various blocks may be divided into additional blocks, combined into fewer blocks, or eliminated, depending on the desired implementation.

In some embodiments, at block 1005, a detection algorithm is implemented, including a calibrated rotation-invariant signal data detection such as that computed using process 800.

In some embodiments, at block 1010, the magnetometer-based metal detection device is maneuvered until a positive detection of a magnetic field indicative of the target metal object is obtained. In some embodiments, the detection of a magnetic field is indicative that the target metal object is nearby to the magnetometer(s) or distal end of the device.

In some embodiments, at block 1015, it is determined whether the magnetic field along one particular axis of the three orthogonal axes of the magnetometer(s) is elevated above the background magnetic field level. The axis sensing the elevated level is then identified.

In some embodiments, at block 1020 the axis sensing an elevated magnetic field is equated with the directionality or directional line along which the target metal object lies. The direction of the axis identified in block 1015 may also be highlighted via the user interface.

Figure 11:
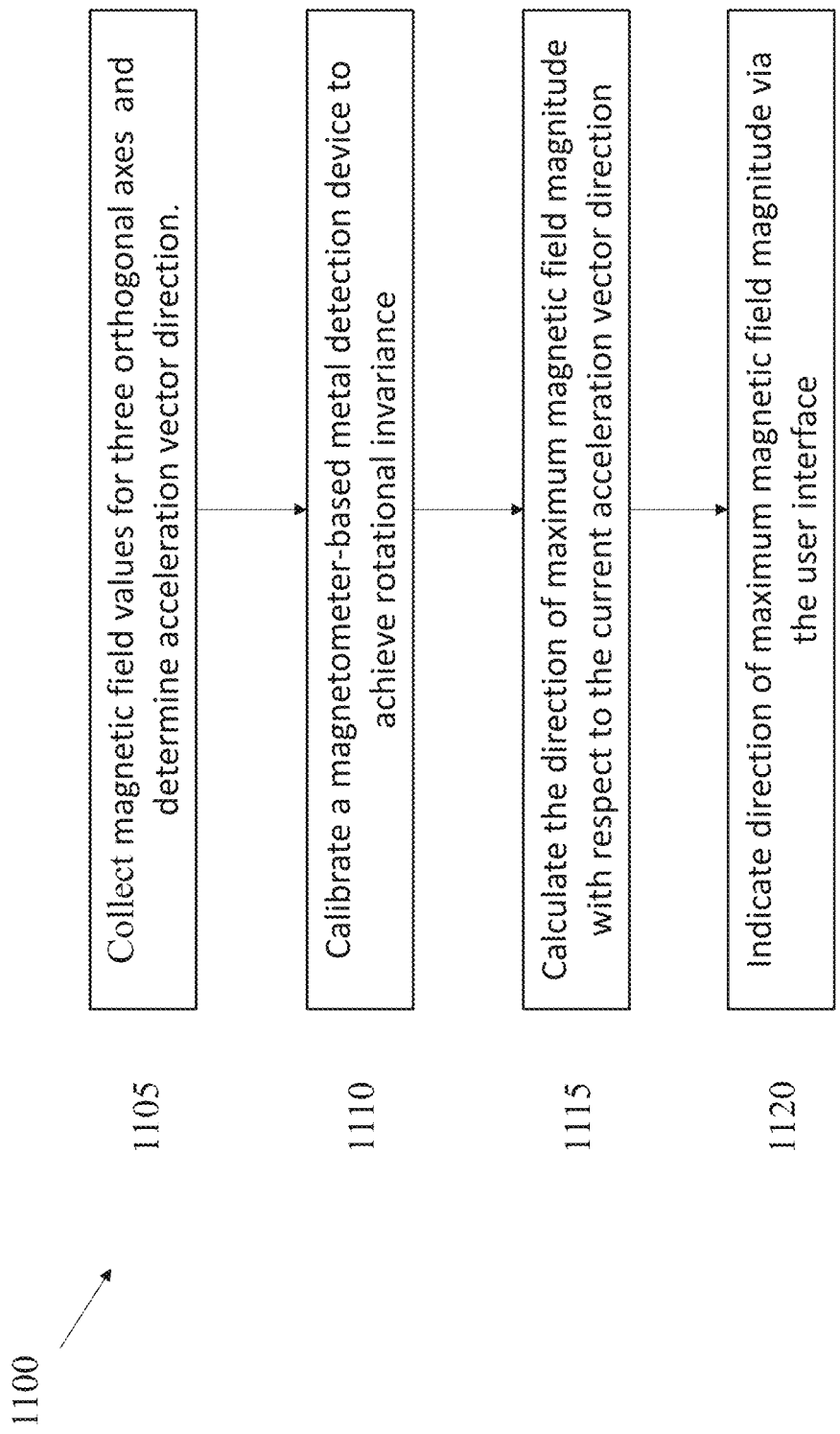
FIG. 11 is a flow chart of an exemplary process for determining the absolute directionality or directional line, with respect to the horizontal plane, along which a target metal object lies.

Referring now to FIG. 11, a flowchart of an exemplary process 1100 for determining an absolute directionality or directional line along which the target metal object lies. In order to determine the absolute direction with respect to the horizontal plane, the orientation of the sensor with respect to the horizontal plane must be determined. Thus, the magnetometer-based metal detection devices may include an accelerometer, which is capable of measuring downward direction of acceleration due to Earth's gravity. This value is then used as a reference from which the relative direction of the local magnetic field can be calculated and displayed via the user interface.

One or more steps of process 1100 may be implemented, in some embodiments, by the magnetometer-based metal detection devices and systems described herein. Although process 1100 is illustrated as discrete blocks, various blocks may be divided into additional blocks, combined into fewer blocks, or eliminated, depending on the desired implementation.

In some embodiments, at block 1105, magnetic field values for three orthogonal axes are collected. Accelerometer sensor data is also collected to determine acceleration vector direction.

In some embodiments, at block 1110, a detection algorithm is implemented, including a calibrated rotation-invariant signal data detection such as that computed using process 800.

In some embodiments, at block 1115, when a magnetic field is detected, (e.g. positive detection) the direction of maximum magnetic field magnitude with respect to the current acceleration vector direction is calculated In some embodiments, at block 1120, the direction of maximum magnetic field magnitude determined at block 1115 is highlighted via the user interface.

In other embodiments, the magnetometer-based metal detection devices and systems described herein are capable of detecting non-magnetic metal objects. For example, devices having two or more sensors (e.g., magnetometer sensors) can be used to increase sensitivity and to increase the data collected on the magnetic field(s), such as how the field(s) vary over space and time. Thus, detecting non-magnetic objects, such as needles or other metal targets that do not generate their own magnetic field, can be achieved via measurement of distortions to preexisting magnetic fields near the sensors. For example, when magnetometer sensors are initially calibrated, very small changes due to these distortions in the preexisting local magnetic field are detectable. In another example, a magnetic field can be generated by the device itself (such as via a permanent magnet or an electromagnet), from which the distortions of the generated magnetic field caused by the non-magnetic target object can be measured or detected. It should be appreciated that measurement of these distortions can be performed for both detection of non-magnetic objects as well as magnetized objects.

In other embodiments, the magnetometer-based metal detection devices and systems described herein are capable of gradient detection by devices having two or more sensors, via obtaining data with respect to the spatial difference in magnetic field magnitude and location. For example, very sensitive positive identification of a target object can occur because the magnetic field near small, weakly magnetized objects varies significantly (i.e., a large spatial gradient), while the background field varies minimally (i.e., a mall spatial gradient).

In still other embodiments, the trajectory of a target can be determined using an array of magnetometer sensors. For example, the sensors map the nearby magnetic field, and because data is collected over time, trends can be determined, such as the trajectory of a target. For example, if a detection event occurs at a first sensor, and then a short time later a detection event occurs at a second sensor, then it can be determined that the target object "moved" (relative to the magnetometer-based metal detection device) past the sensor array in the direction from the position of the first sensor to the position of the second sensor.

In some embodiments, systems or methods for magnetizing a metallic surgical device, such as a needle, prior to use in surgery are included. In some embodiments, a tray that may be sized and configured to hold needles during an operation may be included. The tray may include one or more magnets (e.g., an electromagnets) that may be located and/or positioned on the tray to magnetically couple with the metallic surgical device. The magnetic coupling may permanently or temporarily magnetize the metallic surgical device. The magnetized metallic surgical device, if unfortunately misplaced during surgery, may be discovered or located using the magnetometer-based metal detection devices suitable for detection of magnetized metal objects.

In some embodiments, an electromagnet or permanent magnet positioned in the distal portion of the magnetometer-based metal detection device (FIG. 3) may be used to magnetize metallic objects, for example metallic needles that may be internal to a surgical subject. In some embodiments, other means are used to magnetize metallic objects in situ that are internal to a surgical subject. By doing so, the discovered object can be more easily retrieved via attraction to the same electromagnet or permanent magnet Various embodiments are disclosed. The various embodiments may be partially or completely combined to produce other embodiments.

Numerous specific details are set forth herein to provide a thorough understanding of the claimed subject matter. However, those skilled in the art will understand that the claimed subject matter may be practiced without these specific details. In other instances, methods, apparatuses, or systems that would be readily known by one of ordinary skill in the art have not been described in detail so as not to obscure claimed subject matter.

Some portions are presented in terms of algorithms or symbolic representations of operations on data bits or binary digital signals stored within a computing system memory, such as a computer memory. These algorithmic descriptions or representations are examples of techniques used by those of ordinary skill in the data processing art to convey the substance of their work to others skilled in the art. An algorithm is a self-consistent sequence of operations or similar processing leading to a desired result. In this context, operations or processing involves physical manipulation of physical quantities. Typically, although not necessarily, such quantities may take the form of electrical or magnetic signals capable of being stored, transferred, combined, compared, or otherwise manipulated. It has proven convenient at times, principally for reasons of common usage, to refer to such signals as bits, data, values, elements, symbols, characters, terms, numbers, numerals, or the like. It should be understood, however, that all of these and similar terms are to be associated with appropriate physical quantities and are merely convenient labels. Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical, electronic, or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general-purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in full or in part by the operation of such computing devices. The order of the blocks presented in the examples above can be varied—for example, blocks can be re-ordered, combined, and/or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

Kits

In one aspect, the present invention provides a magnetometer-based metal detection kit comprising instrumentation to magnetize/demagnetize, detect, and retrieve a metal object before, during and after a medical procedure. In some embodiments, the kit comprises the magnetometer-based metal detection device as described herein. In some embodiments, the kit comprises the magnetometer-based metal detection device in addition to a device for magnetizing and/or demagnetizing a metal object. In some embodiments, the magnetizing/demagnetizing device magnetizes/demagnetizes a metal object by applying a current to the metal object. In some embodiments, the magnetizing device is a permanent magnet that magnetizes a metal object by being placed in direct contact with the metal object or by being placed in close proximity to the metal object thereby magnetizing the metal object. Accordingly, kit may include some or all instrumentation required to magnetize/demagnetize, detect, and/or retrieve a metal object during a medical procedure.

In some embodiments, the kit may include one or more magnetometer-based metal detection device in addition to one or more devices for magnetizing and/or demagnetizing a metal object that are packaged. In some embodiments, the one or more components of the kit are sterile packaged. In some embodiments, the one or more components of the kit are contained in one or more individual sterile packages within the kit. The sterile implant kit described herein is thus immediately ready for surgical application upon removal of the components from their respective packages without the need for pre-operation cleaning, sterilizing, or other processing. In certain aspects, the one or more components of the kit are single-use components. For example, in one embodiment, the one or more components of the kit are sterile and disposable. In another embodiment, the one or more components of the kit are repackaged after use, where, in certain embodiments, the one or more components may be reprocessed for future use.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore and are not to be construed as limiting in any way the remainder of the disclosure.

Example 1. Quantifying Needle Magnetization and Detection

In order to evaluate the efficacy of detection of a magnetometer-based metal detection device, a series of experiments were performed to determine the reproducibility of needle magnetization and demagnetization, to quantify the needle magnetization detected by the device as a function of the distance between the needle and sensor, and to determine the needle magnetization as a function of applied magnetic field.

The Materials and Methods Used are Now Described.

Needle magnetization and demagnetization were performed on Ethicon CT-1 needles by placing the entire needle package inside a long solenoid coil and applying current up to 10 Amps DC (magnetization) or 6 Amps AC (demagnetization).

The needle magnetization was measured by fixing the device on a stand, then moving the needle toward the device. Magnetization was recorded as a function of distance between the needle and the device. Additionally, the initial magnetization of the "new" needle was measured as a function of distance, as was as the magnetization of the demagnetized needle. For each series of measurements, demagnetization was carried out before magnetization to reset the magnetization level to baseline. Because the magnetometer detects on all 3 axes, magnetization values were reported as the magnitude: $B=\sqrt{B_x^2+B_y^2+B_z^2}$.

The Results and Conclusions of Experiments are Now Discussed.

Figure 12:
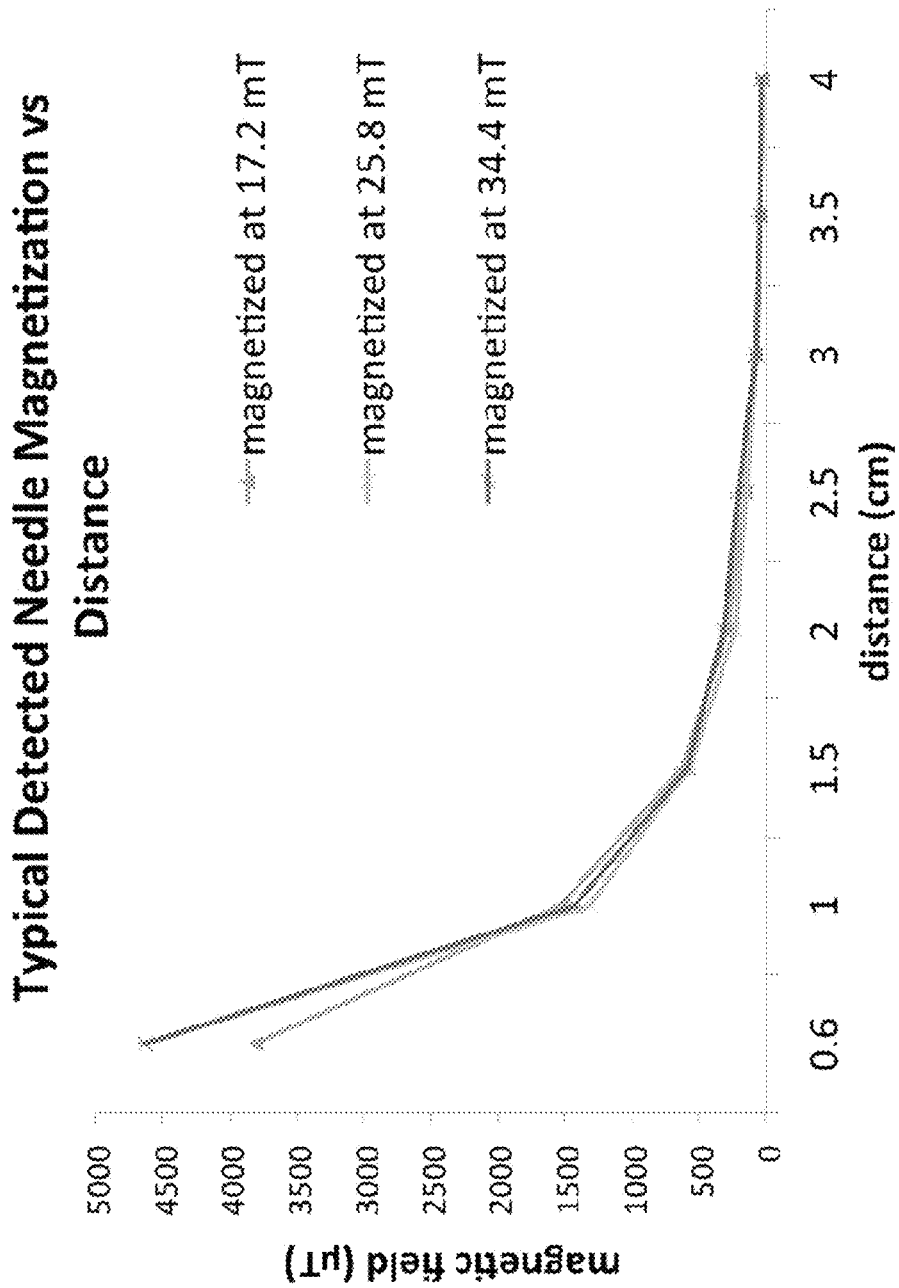
FIG. 12 depicts experimental data evaluating detected needle (metal object) magnetization in microTesla ($\mu$T) with respect to the distance between the needle and sensor in centimeters (cm).
Figure 13:
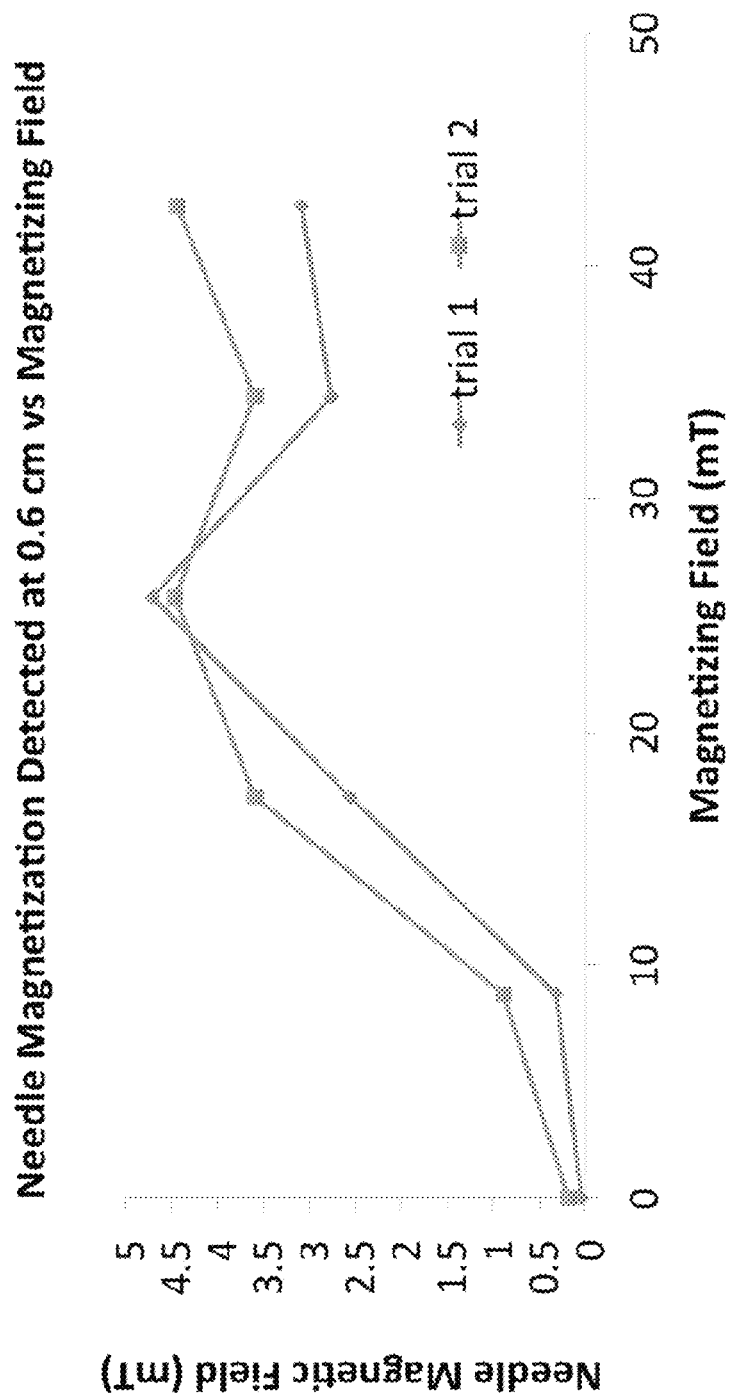
FIG. 13 depicts experimental data evaluating the magnetization in milliTesla (mT) of the detected needle (metal object) when the needle is 0.6 cm from the sensor with respect to the strength of the magnetizing field in milliTesla (mT).

Magnetized CT-1 needles were determined to be within the detectable range of the device, that being approximately between 3 cm and 4 cm, as depicted in FIG. 12. Comparing the results measured at 1 cm distance, magnetization appears to saturate at around 20 milliTesla (mT). That is, the needle had the same magnetization at 20 mT as it did at 25 mT and 30 mT. Needle magnetization appears to be reproducible from one needle to the next, and for the same needle after demagnetization, as illustrated in FIG. 13.

Furthermore, it was determined that the needle magnetization level can be controlled as a function of applied current/field.

While the present subject matter has been described in detail with respect to specific embodiments thereof, it will be appreciated that those skilled in the art, upon attaining an understanding of the foregoing, may readily produce alterations to, variations of, and equivalents to such embodiments. Accordingly, it should be understood that the present disclosure has been presented for-purposes of example rather than limitation, and does not preclude inclusion of such modifications, variations, and/or additions to the present subject matter as would be readily apparent to one of ordinary skill in the art.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A magnetometer-based medical metal detection device comprising:
   a proximal portion, a rigid central body and a flexible and adjustable distal portion;
   at least two magnetometers positioned in or on the distal portion, wherein a first magnetometer and second magnetometer of the at least two magnetometers are single-axis magnetometers, wherein each of the at least two magnetometers includes at least one magnetic field sensor, and wherein the rigid central body comprises a tube having a circular outer cross-section, a diameter between 2 and 20 mm, and a length between 1 and 60 cm;
   a processor configured to:
     receive magnetic field data from the first magnetometer and the second magnetometer;
     filter the magnetic field data to remove background noise from the magnetic field data, wherein the background noise includes earth's magnetic field data over time;
     calculate a moving average of the filtered magnetic field data from the first magnetometer and the second magnetometer;
     compare the moving average of the filtered magnetic field data to a threshold value;
     determine when the moving average of the filtered magnetic field data is greater than a threshold value; and
     calculate a trajectory of a non-magnetized metal object in a body of a subject based on measurements by the first magnetometer and the second magnetometer of distortions to a magnetic field relative to the detection device in the body of the subject;
   wherein the non-magnetized metal object comprises a surgical object; and
   an indicator, wherein the processor is configured to turn on the indicator when the moving average of the filtered magnetic field data from the first magnetometer and the second magnetometer is greater than the threshold value, and indicate proximity of the non-magnetized metal object relative to the detection device when the indicator is turned on.

2. The device of claim 1, further comprising an actuator positioned in or on the proximal portion, wherein the actuator is capable of directing movement of the flexible and adjustable distal portion.

3. The device of claim 1, further comprising an accelerometer positioned in or on the distal portion.

4. The device of claim 1, further comprising a permanent magnet positioned in or on the distal portion.

5. The device of claim 1, further comprising an electromagnet positioned in or on the distal portion.

6. The device of claim 1, further comprising a user interface communicatively connected to the processor.

7. The device of claim 6, further comprising a memory and programming logic resident on the memory, wherein the programming logic is capable of calibrating the device to achieve rotational invariance.

8. The device of claim 7, wherein the programming logic is further capable of determining a directionality or directional line along which the non-magnetized metal object lies.

9. The device of claim 8, further comprising an accelerometer in or on the distal portion, and wherein the programming logic is further capable of determining an absolute directionality or directional line, with respect to a horizontal plane, along which the target metal object lies.

10. The device of claim 1, further comprising at least one magnet capable of magnetizing the non-magnetized metal object in situ.

11. The device of claim 1, further comprising a modulator capable of adjusting a sensitivity of the at least two magnetometers.

12. The device of claim 1, wherein the indicator is selected from a group consisting of an indicator light and a sound emitting device.

13. A magnetometer-based medical metal detection device comprising:
a proximal portion comprising a grasping handle;
a rigid central body comprising a hollow tube having a lumen, wherein the hollow tube is from 10 cm to 60 cm long and 2 mm to 20 mm in diameter;
a flexible and adjustable distal portion comprising an accelerometer and two magnetometers;
wherein a first and second of the at least two magnetometers are single-axis magnetometers;
a processor configured to:
receive magnetic field data from the first magnetometer and the second magnetometer;
filter the magnetic field data to remove background noise from the magnetic field data, wherein the background noise includes earth's magnetic field data over time;
calculate a moving average of the filtered magnetic field data from the first magnetometer and the second magnetometer;
compare the moving average of the filtered magnetic field data to a threshold value;
determine when the moving average of the filtered magnetic field data is greater than a threshold value; and
calculate a location of a non-magnetized metal object relative to the detection device, wherein the non-magnetized metal object comprises a surgical object in a body of a subject;
an indicator light, wherein the processor is configured to turn on the indicator when the moving average of the filtered magnetic field data from the first magnetometer and the second magnetometer is greater than the threshold value, and indicate the location of the non-magnetized metal object relative to the detection device when the indicator is turned on; and
a control actuator extending through the lumen, wherein the control actuator comprises a cable and wires extending through the lumen from the proximal portion to the distal portion;
wherein when the cable is in a first position, the distal portion is in line with a central axis of the rigid central body, and when the cable is in a second position, the distal portion flexibly curves so the distal portion is out of line with the central axis of the rigid central body, and wherein the proximal portion comprises a first mechanical modulator for manipulating a position of the distal portion via the cable.

14. The device of claim 13, wherein the distal portion is extendable out of the lumen, and wherein the proximal portion comprises a second mechanical modulator for manipulating the position of the distal portion.

15. The device of claim 13, wherein the indicator is selected from a group consisting of an indicator light and a sound emitting device.

16. A magnetometer-based medical metal detection device comprising:
a proximal portion, a rigid central body and a flexible and adjustable distal portion;
at least two magnetometers positioned in or on the distal portion, wherein a first magnetometer and second magnetometer of the at least two magnetometers are multi-axis magnetometers, wherein each of the at least two magnetometers includes at least one magnetic field sensor, and wherein the rigid central body comprises a tube having a circular outer cross-section, a diameter between 2 and 20 mm, and a length between 1 and 60 cm;
a processor configured to:
receive magnetic field data from the first magnetometer and the second magnetometer;
filter the magnetic field data to remove background noise from the magnetic field data, wherein the background noise includes earth's magnetic field data over time;
calculate a moving average of the filtered magnetic field data from the first magnetometer and the second magnetometer;
compare the moving average of the filtered magnetic field data to a threshold value;
determine when the moving average of the filtered magnetic field data is greater than a threshold value; and
calculate a trajectory of a non-magnetized metal object in a body of a subject based on measurements by the first magnetometer and the second magnetometer of distortions to a magnetic field relative to the detection device in the body of the subject;
wherein the non-magnetized metal object comprises a surgical object; and
an indicator, wherein the processor is configured to turn on the indicator when the moving average of the filtered magnetic field data from the first magnetometer and the second magnetometer is greater than the threshold value, and indicate a directional line along which the non-magnetized metal object lies when the indicator is turned on.

17. The device of claim 16, wherein the indicator is selected from a group consisting of an indicator light and a sound emitting device.

* * * * *